United States Patent [19]

Tanaka et al.

[11] Patent Number: 4,698,177
[45] Date of Patent: Oct. 6, 1987

[54] CYCLOHEXYLCYCLOHEXENE DERIVATIVES

[75] Inventors: Yasuyuki Tanaka, Tokyo; Haruyoshi Takatsu, Kodaira; Kiyohumi Takeuchi, Tokyo, all of Japan

[73] Assignee: Dainippon Ink and Chemicals, Inc., Tokyo, Japan

[21] Appl. No.: 850,585

[22] Filed: Apr. 11, 1986

[30] Foreign Application Priority Data

Apr. 16, 1985 [JP] Japan .................................. 60-79239
May 27, 1985 [JP] Japan ................................. 60-113597

[51] Int. Cl.$^4$ ...................... C07C 13/00; C09K 19/30
[52] U.S. Cl. ........................... 252/299.63; 252/299.5; 252/299.6; 350/350 R; 350/350 S; 585/20; 585/23
[58] Field of Search ............. 252/299.63, 299.5, 299.6; 350/350 R, 350 S; 585/23, 20

[56] References Cited

U.S. PATENT DOCUMENTS

| | | | |
|---|---|---|---|
| 4,211,666 | 7/1980 | Inukai et al. | 252/299.6 |
| 4,386,007 | 5/1983 | Krause et al. | 252/299.62 |
| 4,422,951 | 12/1983 | Sugimori et al. | 252/299.63 |
| 4,505,837 | 3/1985 | Romer et al. | 252/299.6 |
| 4,510,069 | 4/1985 | Eidenschink et al. | 252/299.63 |
| 4,594,465 | 6/1986 | Cham et al. | 252/299.66 |
| 4,622,164 | 11/1986 | Eidenschink et al. | 252/299.63 |

FOREIGN PATENT DOCUMENTS

| | | | |
|---|---|---|---|
| 3321373 | 12/1984 | Fed. Rep. of Germany | 252/299.63 |
| 3510434 | 9/1986 | Fed. Rep. of Germany | 252/299.63 |
| 57-4927 | 1/1982 | Japan | 252/299.6 |
| 57-11935 | 1/1982 | Japan | 252/299.6 |
| 59-110641 | 6/1984 | Japan | 252/299.63 |
| 60-64935 | 4/1985 | Japan | 252/299.6 |
| 60-69059 | 4/1985 | Japan | 252/299.63 |
| 2078727 | 1/1982 | United Kingdom | 252/299.6 |

*Primary Examiner*—Teddy S. Gron
*Attorney, Agent, or Firm*—Sherman and Shalloway

[57] ABSTRACT

A compound represented by the general formula

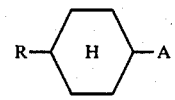

wherein R denotes a linear alkyl group having 1 to 9 carbon atoms, A denotes

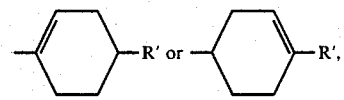

denotes a linear alkyl group having 1 to 9 carbon atoms, and each cyclohexane ring is arranged in a trans-(equatorial-equatorial) form.

8 Claims, No Drawings

CYCLOHEXYLCYCLOHEXENE DERIVATIVES

This invention relates to nove cyclohexyl cuyclohexene derivatives useful as electro-optical display materials.

Typical liquid crystal display cells include, for example, a field effect mode cell proposed by M. Schadt et al. [Applied Physics Letters, 18, 127–128 (1971)], a dynamic scattering mode cell proposed by G. H. Heilmeier [Proceddings of the I.E.E.E., 56, 1162–1171 (1968)], and a guest-host mode cell proposed by G. H. Heilmeier [Applied Physics Letters, 13, 91 (1968)] or D. L. White, et al. [Journal of Applied Physics, 45, 4718 (1974)].

Liquid crystalline materials used in these liquid crystal display cells are required to have various properties. Above all, a high-speed response at low temperatures is required of liquid crystalline display cells used outdoors.

A response time (t) is in proportion to a viscosity ($\eta$) of liquid crystalline materials (t $\propto$ $\eta$). Accordingly, when using liquid crystalline materials having a low viscosity at low temperature, liquid crystalline display cells with a high-speed response at low temperatures can be produced.

A quite excellent viscosity reducing agent used at formula

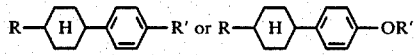

(wherein R and R' each denote a linear alkyl group). However, the compound represented by the formula

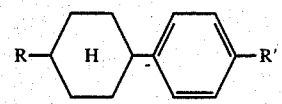

is quite high in effect of reducing the viscosity, but notably decreases the N-I transition temperatures. The compound represented by the formula

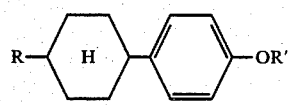

does not so much decrease the N-I transition temperatures, but gives no sufficient effect of reducing the viscosity.

An object of this invention is to provide a compound having a high effect of reducing a viscosity but less decreasing the N-I transition temperatures.

As a compound capable of achieving this object, the present invention provides a compound represented by the general formula

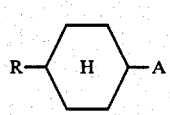

wherein R denotes a linear alkyl group having 1 to 9 carbon atoms, A denotes

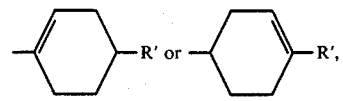

R' denotes a linear alkyl group having 1 to 9 carbon atoms, and each cyclohexane ring is arranged in a trans-(equatorial-equatorial) form.

The compound (I-1) of the formula (I) wherein A is

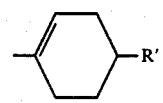

can be produced in the following process.

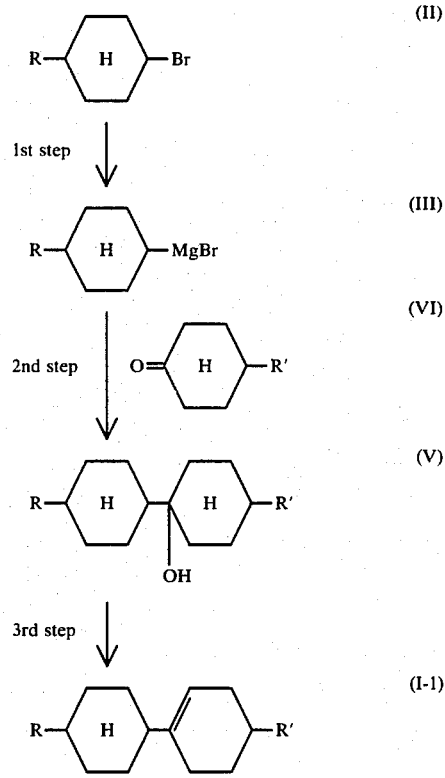

wherein R and R' have the same meanings as in the formula (I).

1ST STEP

The trans-4-n-alkyl-1-bromocyclohexane of the formula (II) is reacted with a magnesium powder in anhydrous ether or anhydrous tetrahydrofuran to form an anhydrous ether or anhydrous tetrahydrofuran solution of the compound of the formula (III).

2ND STEP

The anhydrous ether or anhydrous tetrahydrofuran solution of the compound of the formula (III) formed in the 1st step is reacted with the 4-n-alkyl-cyclohexanone of the formula (IV), and the reaction mixture is then decomposed with hydrochloric acid to form the compound of the formula (V).

3RD STEP

The compound of the formula (V) formed in the 2nd stage is dehydrated with p-toluenesulfonic acid in a solvent such as toluene to form the compound of the formula (I-1).

The compound (I-2) of the formula (I) wherein A is

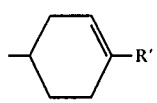

can be produced in the following process.

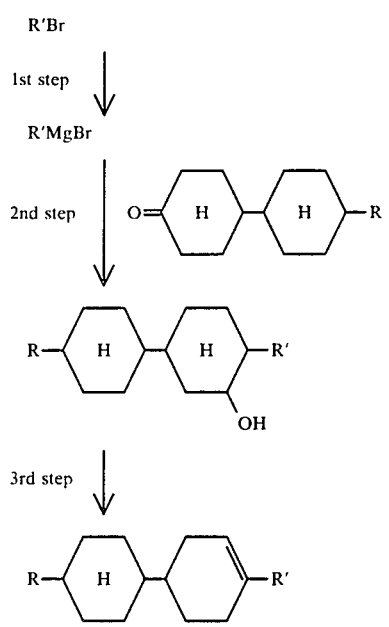

wherein R and R' have the same meanings as in the formula (I).

1ST STEP

The n-alkyl bromide of the formula (VI) is reacted with a magnesium powder in anhydrous ether or anhydrous tetrahydrofuran to form an anhydrous ether or anhydrous tetrahydrofuran solution of the compound of the formula (VII).

2ND STEP

The anhydrous ether or anhydrous tetrahydrofuran solution of the compound of the formula (VII) formed in the 1st step is reacted with the 4-(4'-n-alkylcyclohexyl)cyclohexanone of the formula (VIII), and the reaction mixture is then decomposed with hydrochloric acid to form the compound of the formula (IX).

3RD STEP

The compound of the formula (IX) formed in the 2nd step is dehydrated with p-toluenesulfonic acid in a solvent such as toluene to form the compound of the formula (I-2).

The typical compounds of the formula (I) thus formed have transition temperatures shown in Table 1.

TABLE 1

| No. | Compounds of formula (I) | Transition temperatures (°C.) |
|---|---|---|
| 1 | n-$C_3H_7$—(H)—( )—n-$C_3H_7$ | −3° C. (C⇌N) 15° C. (N⇌I) |
| 2 | n-$C_3H_7$—(H)—( )—n-$C_7H_{15}$ | 29° C. (C⇌S) 36° C. (S⇌N) 39° C. (N⇌I) |
| 3 | n-$C_3H_7$—(H)—( )—n-$C_5H_{11}$ | −11° C. (C⇌S) 12° C. (S⇌N) 27° C. (N⇌I) |
| 4 | n-$C_5H_{11}$—(H)—( )—n-$C_3H_7$ | 4° C. (C⇌S) 21° C. (S⇌N) 30° C. (N⇌I) |
| 5 | N—$C_3H_7$—(H)—( )—n-$C_3H_7$ | 26° C. (C⇌I) |
| 6 | n-$C_3H_7$—(H)—( )—n-$C_5H_{11}$ | −10° C. (C⇌S) 19° C. (S⇌N) 22° C. (N⇌I) |

The compounds of the formula (I) in accordance with this invention are nematic liquid crystal compounds having a weak positive dielectric anisotropy and can therefore be used, for example, as materials for dynamic scattering mode cells in the form of mixtures with other nematic liquid crystalline compounds having a negative or weak positive dielectric anisotropy, or as materials for field effect mode display cells in the form of mixtures with other nematic liquid crystal compounds having a strong positive dielectric anisotropy.

Typical examples of the nematic liquid crystalline compounds which can preferably be used in admixture with the compounds of the formula (I) include 4'-substituted phenyl 4-substituted benzoates, 4'-substituted phenyl 4-substituted cyclohexanecarboxylates, 4'-substituted biphenyl 4-substituted cyclohexanecarboxylates, 4'-substituted phenyl 4-(4-substituted cyclohexanecarbonyloxy) benzoates, 4'-substituted phenyl 4-(4-substituted cyclohexyl) benzoates, 4'-substituted cylohexyl 4-(4-substituted cyclohexy) benzoates, 4,4'-substituted biphenyl, 4-substituted phenyl 4'-substituted cyclohexane, 4,4'-substituted terphenyl, 4-substituted biphenyl 4'-substituted cyclohexane and 2-(4-substituted phenyl)-5-substituted pyrimidine.

Table 2 shows the viscosities at 0° C. and 20° C. and the N-I points measured for the mixed liquid crystals composed of 75% by weight of the below-described matrix liquid crystals (A) now in widespread use as nematic liquid crystalline materials and 25% by weight of the compounds Nos. 1 to 6 of the formula (I) shown in Table 1. The same table also shows, for comparison, the viscosities at 0° C. and 20° C. and the N-I points measured for the matrix liquid crystals (A) and the mixed liquid crystals composed of 75% by weight of the matrix liquid crystals (A) and 25% by weight of the below-described compounds (a) and (b).

The matrix liquid crystals (A) comprise

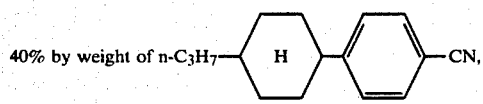
40% by weight of n-C₃H₇—〈H〉—〈 〉—CN,

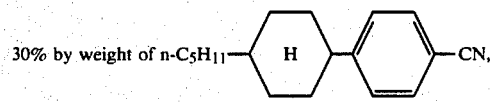
30% by weight of n-C₅H₁₁—〈H〉—〈 〉—CN, and

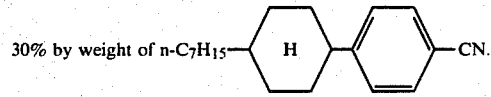
30% by weight of n-C₇H₁₅—〈H〉—〈 〉—CN.

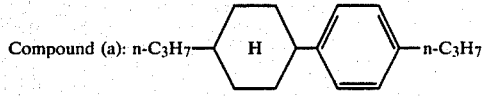
Compound (a): n-C₃H₇—〈H〉—〈 〉—n-C₃H₇

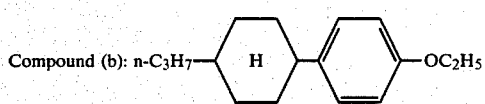
Compound (b): n-C₃H₇—〈H〉—〈 〉—OC₂H₅

TABLE 2

|  | Viscosity (c.p.) at 20° C. | Viscosity (c.p.) at 0° C. | N-I point (°C.) |
|---|---|---|---|
| (A) | 22.0 | 72.2 | 51.2 |
| (A) + No. 1 | 15.3 | 41.5 | 41.4 |
| (A) + No. 2 | 17.5 | 50.5 | 43.5 |
| (A) + No. 3 | 16.2 | 44.2 | 42.5 |
| (A) + No. 4 | 16.3 | 44.6 | 42.9 |
| (A) + No. 5 | 16.0 | 44.4 | 40.6 |
| (A) + N0. 6 | 17.2 | 47.8 | 41.2 |
| (A) + (a) | 17.5 | 40.2 | 26.0 |
| (A) + (b) | 16.8 | 48.3 | 43.0 |

From Table 2, it can be seen that the compounds Nos. 1-6 of this invention markedly reduce the viscosity of the matrix liquid crystals but do not decrease the N-I point thereof so much. Comparison of the compounds No. 1, (a) and (b) approximately equal in length of the terminal alkyl or alkoxy group reveals that with respect to the effect of reducing the viscosity at 0° C. the compound No. 1 is the same as the compound (a) and quite high, and with respect to the decrease in N-I point, the compound No. 1 is the same as the compound (b) and relatively small. From these facts, it becomes apparent that the compound No. 1 has both the excellent properties of the compound (a) and (b).

EXAMPLE 1

24.3g (0.119 mol) of trans-4-n-propyl-1-bromocyclohexane was dissolved in 96 ml of anhydrous tetrahydrofuran, and with stirring the solution was added dropwise to 3.0g (0.123g - atm) at 20° C. to 30° C. Subsequently, the mixture was reacted at room temperature (25° C.) for 2 hours to form trans-4-n-propylcyclohexyl-magesium bromide.

Thereafter, 23.3g (0.119 mol) of 4-n-heptylcyclohexan-1-one was dissolved in 23 ml of anhydrous tetrahydrofuran. The solution was added dropwise in an anhydrous tetrahydrofuran solution of the above obtained trans-4-n-propylcyclohexylmagnesium bromide at room temperature (25° C.) with stirring, followed by reacting the mixture at a reflux temperature for 3 hours.

The reaction mixture was poured into a cold dilute hydrochloric acid, and the reaction product was extracted with ether. The extract was washed with water and dried, and ether was evaporated from the solution to obtain 39.7g of a coarse product containing a compound of the following formula.

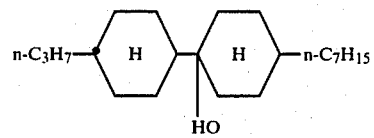
n-C₃H₇—〈H〉—〈H〉—n-C₇H₁₅
           |
          HO

The coarse product was dissolved in 200 ml of xylene, and 1.13g (0.00595 mol) of p-toluenesulfonic acid monohydrate was added to the solution. With stirring, the mixture was reacted at a reflux temperature for 3 hours.

After the reaction mixture was cooled, the reaction product was extracted with xylene. The extract was washed with water and dried, and xylene was then evaporated from the solution. The resulting reaction product was purified by chromatography on a column of silica gel and further recrystallized from ethanol containing a small amount of n-hexane to afford 15.2 g (0.0500 mol) of a compound of the following formula.

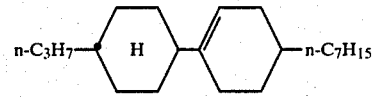
n-C₃H₇—〈H〉—〈 〉—n-C₇H₁₅

Yield: 42.0%.
Transition temperatures:
29.0° C. (C→S)
36.0° C. (S→N)
39.4° C. (N→I).

EXAMPLE 2

A compound of the following formula was obtained in the same way as in Example 1.

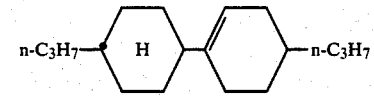
n-C₃H₇—〈H〉—〈 〉—n-C₃H₇

Yield: 37.2%.
Transition temperatures:
−3° C. (C→N)
15° C. (N⇌I).

EXAMPLE 3

A compound of the following formula was obtained in the same way as in Example 1.

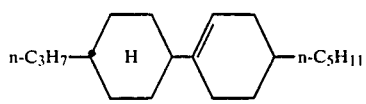

Yield: 39.0%.
Transition temperatures:
−11° C. (C→S)
12° C. (S⇌N)
27° C. (N⇌I).

EXAMPLE 4

A compound of the following formula was obtained in the same way as in Example 1:

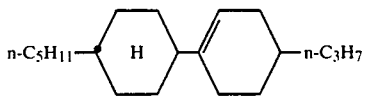

Yield: 38.5%.
Transition temperatures:
4° C. (C→S)
21° C. (S⇌N)
30° C. (N⇌I).

EXAMPLE 5

8.20 g (0.0543 mol) of n-pentyl bromide was dissolved in 41 ml of anhydrous tetrahydrofuran, and with stirring the solution was added dropwise to 1.40g (0.0576 g-atm) of magnesium at room temperature (b 25° C.) for 1 hour to form n-pentylmagesium bromide.

Subsequently, 10.0 g (0.0450 mol) of a compound of the formula

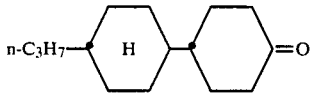

was dissolved in 20 ml of anhydrous tetrahydrofuran, and the solution was added dropwise to an anhydrous tetrahydrofuran solution of the above obtained n-penthylmagnesium bromide at 10° to 20° C. with stirring. The mixture was then reacted at room temperature (25° C.) for 2 hours and further at 40° C. to 50° C. for 3 hours.

After cooling, the reaction mixture was poured into a cold dilute hydrochloric acid, and the reaction product was extracted with ether. The extract was washed with water and dried, and ether was then evaporated from this solution to afford 14.7 g of a coarse product containing a compound of the following formula.

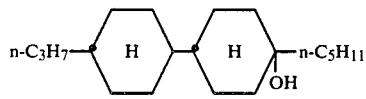

The coarse product was dissolved in 120 ml of toluene, and 0.3 g (0.00158 mol) of p-toluenesulfonic acid monohydrate was added to the solution. With stirring, the mixture was then reacted at a reflux temperature for 2 hours.

After the reaction mixture was cooled, a toluene layer was washed with water and dried, and toluene was then evaporated from the solution. The resulting reaction product was purified by chromatography on a column of a silica gel and further recrystallized from ethanol containing a small amount of n-hexane to obtain 7.56 g (0.0274 mol) of a compound of the following formula.

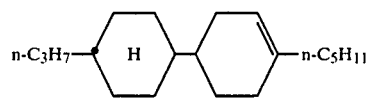

Yield: 60.9%.
Transition temperatures:
−10° C. (C→S)
19° C. (S⇌N)
22° C. (N⇌I).

EXAMPLE 6

A compound of the following formula was obtained in the same way as in Example 5.

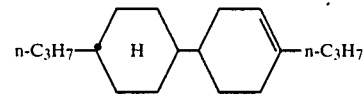

Yield: 50.7%
Transition temperature: 26° C. (C→I).

The compounds of formula (I) in accordance with this invention, when added to the matrix liquid crystals, provide a high effect of reducing the viscosity but do not decrease the N-I transition temperatures so much. Said effect of reducing the viscosity is as high as that of the compounds of the formula

which have been so far known as a viscosity reducing agent with the excellent effect of reducing the viscosity. Moreover, the decrease in N-I point thereof is as small as that of the compounds of the formula

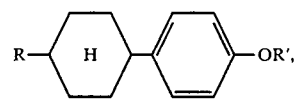

which have been so far known as a viscosity reducing agent to less decrease the N-I point. Accordingly, the compounds of the formula (I) in this invention are those having both the properties of these known compounds.

What we claim is:

1. A nematic liquid crystalline composition for electro-optical display materials comprising a mixture of matrix liquid crystals and at least one viscosity-reducing agent represented by the formula

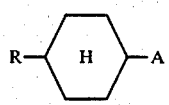

wherein R denotes a linear alkyl group having 1 to 9 carbon atoms, A denotes

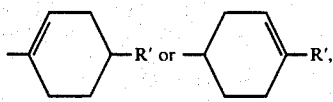

R' denotes a linear alkyl group having 1 to 9 carbon atoms and each cyclohexane ring is arranged in a trans(equatorial-equatorial) form.

2. The composition of claim 1 wherein the viscosity-reducing agent is

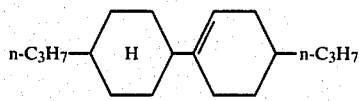

3. The composition of claim 1 wherein the viscosity-reducing agent is

4. The composition of claim 1 wherein the viscosity-reducing agent is

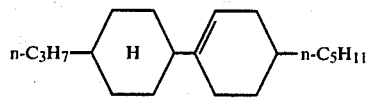

5. The composition of claim 1 wherein the viscosity-reducing agent is

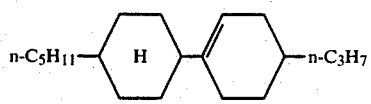

6. The composition of claim 1 wherein the viscosity-reducing agent is

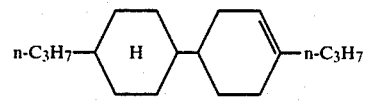

7. The composition of claim 1 wherein the viscosity-reducing agent is

8. The composition of claim 1 wherein the matrix liquid crystals are at least two nematic liquid crystalline compounds selected from the group consisting of 4'-substituted phenyl 4-substituted benzoated, 4'-substituted phenyl 4-substituted cyclohexanecarboxylates, 4'-substituted biphenyl 4-substituted cyclohexanecarboxylates, 4'-substituted phenyl 4-(4-substituted cyclohexanecarbonyloxy)-benzoates, 4'-substituted phenyl 4-(4-substituted cyclohexyl) benzoates, 4'-substituted cyclohexyl 4-(4-substituted cyclohexyl) benzotes, 4,4'-substituted biphenyl, 4-substituted phenyl 4'-substituted cyclohexane, 4,4''-substituted terphenyl, 4-substituted biphenyl 4''-substituted cyclohexane and 2-(4-substituted phenyl)-5-substituted pyrimidine.

* * * * *

UNITED STATES PATENT AND TRADEMARK OFFICE
CERTIFICATE OF CORRECTION

PATENT NO. : 4,698,177
DATED : October 6, 1987
INVENTOR(S) : YASUYUKI TANAKA, ET AL.

It is certified that error appears in the above-identified patent and that said Letters Patent is hereby corrected as shown below:   Title page:

IN THE ABSTRACT

Line 3 from the bottom, before "denotes", insert --R'--.

In the Claims

Column 10, line 35, Claim 8, delete "benzoated", insert --benzoates--.

Signed and Sealed this

Fifth Day of April, 1988

Attest:

DONALD J. QUIGG

Attesting Officer

Commissioner of Patents and Trademarks